United States Patent [19]

Cantor et al.

[11] Patent Number: 4,473,452

[45] Date of Patent: Sep. 25, 1984

[54] ELECTROPHORESIS USING ALTERNATING TRANSVERSE ELECTRIC FIELDS

[75] Inventors: Charles R. Cantor; David C. Schwartz, both of New York, N.Y.

[73] Assignee: The Trustees of Columbia University in the City of New York, New York, N.Y.

[21] Appl. No.: 442,580

[22] Filed: Nov. 18, 1982

[51] Int. Cl.³ .................. G01N 27/26; G01N 27/28
[52] U.S. Cl. ....................... 204/180 G; 204/180 R; 204/299 R
[58] Field of Search ............ 204/180 G, 299 R, 180 R

[56] References Cited

U.S. PATENT DOCUMENTS 4,148,703  4/1979  Trop et al. .................. 204/299 R Primary Examiner—John F. Niebling
Assistant Examiner—B. J. Boggs, Jr.
Attorney, Agent, or Firm—John P. White; Ivan S. Kavrukov

[57] ABSTRACT

Disclosed are an apparatus for and a method of electrophoretically separating particles by electric fields which are transverse to each other, which alternate between respective high and low intensities out of phase with each other at a frequency related to the mass of the particles and which move the particles in an overall direction transverse to the respective directions of the fields. For separating large macromolecules, at least one of the fields preferably has an intensity gradient in a direction transverse to its own. The new arrangement makes it possible to: (1) separate particles (molecules) larger in size than those able to be separated with previously known techniques, (2) carry out separation at higher speed and at better resolution than is possible with previously known techniques, and (3) concurrently separate particles which differ greatly in mass (molecular weight).

26 Claims, 14 Drawing Figures

M1<M2<M3<M4

Fig. 11.
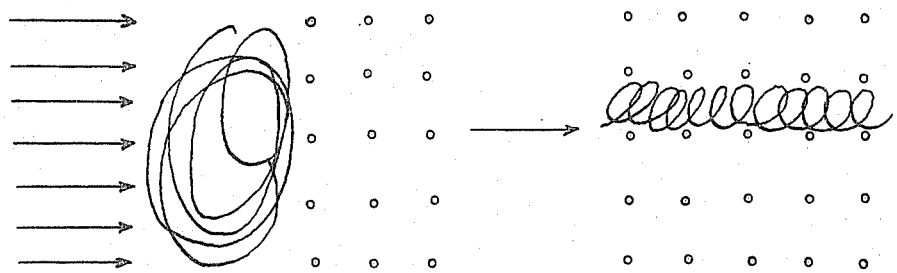
Fig. 12.
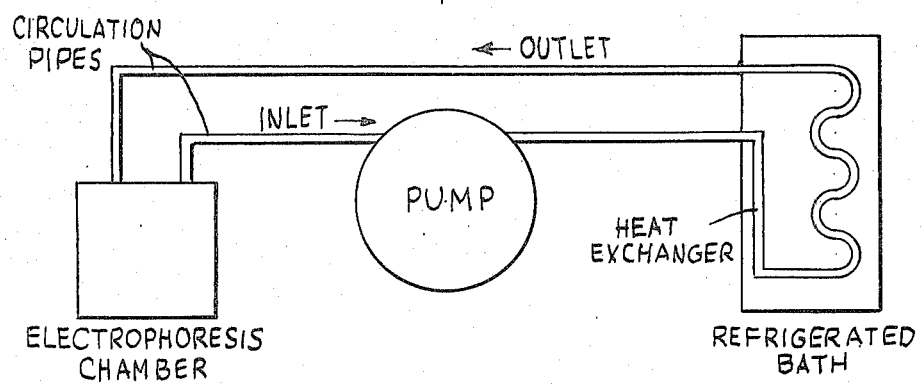
Fig. 13.
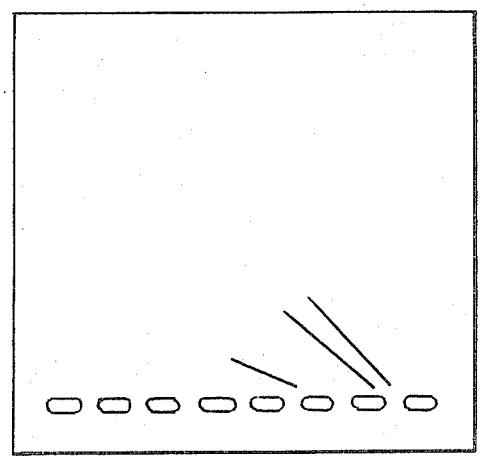
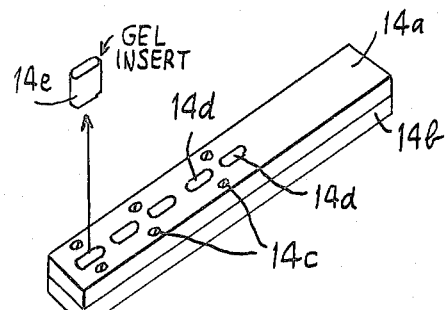
Fig. 14.

ELECTROPHORESIS USING ALTERNATING TRANSVERSE ELECTRIC FIELDS

BACKGROUND AND SUMMARY OF THE INVENTION

This invention was made with government support under Contract No. GM14825 awarded by the National Institutes of Health of the United States Department of Health and Welfare. The government has certain rights in this invention.

The invention is in the field of electrophoresis. It is of particular interest in terms of its applications in genetic engineering and molecular biology.

The invention which is based upon the discovery of a new kind of electrophoresis makes it possible, inter alia, to carry out important analyses which were not possible or practical with previously known techniques. Potential applications include the separation of chromosomal DNA, chromosomal mapping, the convenient production of genetic libraries, studies on the effects of various drugs on chromosomal DNA, and the convenient characterization of polymers. The invention makes it possible to separate with a high degree of resolution and at high speeds larger particles (molecules) than those capable of resolution with prior art techniques, to concurrently separate particles which differ substantially in mass. In a preferred embodiment the invention makes it possible to lyse cells for electrophoretic separation of macromolecules contained in the cells with minimal degradation or breakage.

Electrophoresis in which particles such as a mixture of macromolecules are moved, e.g., through a gel matrix, by an electric field, is a widely used technique for qualitative analysis and for separation, recovery and purification. It is particularly important in the study of proteins, nucleic acids and chromosomes. See, e.g., Cantor, C. R. et al., *Biophysical Chemistry*, Freeman, 1980, Part 2, pp. 676, 683. Indeed, it is probably the principal tool used in most DNA and chromosomal analysis.

Difficulties arise when electrophoretic separation of very large particles is attempted. For example, using previously known techniques, the size of the largest DNA molecule routinely handled is that of a bacteriophage ($3.2 \times 10^7$ daltons). Such a limit on size prevents many kinds of desirable analyses from being carried out. For example, intact chromosomal DNAs are larger and are typically reduced in size in order to make it possible to work with them. This, however, destroys important information encoded within the DNA and precludes many important experiments.

It has been proposed to extend gel electrophoresis to particles of higher mass by reducing the gel concentrations. However, this adversely affects resolution, makes experimental conditions difficult to control and has not been successfully applied to DNA molecules having molecular weights greater than about $5 \times 10^8$ daltons. Fangman, W. L., *Nucleic Acids Research*, Vol. 5, No. 3, March 1978, pp. 653-655; Serwer, P., et al., *Electrophoresis*, 1981, Walter, deGreuyter and Coe, pp. 237-243.

It is believed that resolution in previously known electrophoresis techniques is field-dependent since lower electric field intensities generally give higher resolution. As a consequence, electrophoresis runs in which higher resolution is desired often take as long as 100 hours. Moreover, particle mobility, and hence resolution capability, is believed to vary with the logarithm of the mass of the particles to be separated, which of course is not a highly sensitive basis for obtaining separations. Additionally, in known prior art gel electrophoresis, different gel concentrations are typically used for different mass or molecular weight ranges, thereby limiting the range of particles which can be concurrently resolved. Furthermore, previously known electrophoresis techniques are typically used to separate only small amounts of particles, and the process cannot conveniently be extended to larger amounts.

Despite the fact that electrophoresis has been used for some time, and despite the fact that important limitations thereof and the need to overcome them have also been long known, no previous proposals are known which have successfully overcome such limitations.

This invention is a significant departure from the established principles of electrophoresis and is based on the surprising discovery that electrophoresis through deliberately varied electric fields, rather than through the uniform fields sought in previously known electrophoresis methods, unexpectedly yields highly desirable results. More specifically, the invention is based on the discovery that desirable separation results when particles are subjected to respective electrical fields which move them in overall directions generally transverse to the respective general directions of the fields. Particularly desirable results are achieved in at least those cases examined to date when at least one of the electric fields has a deliberate intensity gradient in a direction transverse to its own. As a specific nonlimiting example, two fields can be used which alternate between respective high and low intensities out of phase with each other and are in directions transverse to each other. For example, one of the fields can be on while the other one is off, etc. Particularly good results are obtained when the on and off times of the fields are related to the mass of the particles to be separated, e.g., when the on and off periods are proportional to the mass of the particles raised to a power of about 1.5.

One of the important advantages of this discovery is that it dramatically extends the mass range of particles which can be electrophoretically separated at high resolution. As a nonlimiting example, the new technique can separate at high resolution particles whose mass is about $1.2 \times 10^9$ daltons, while the upper limit of previously known methods which provide lower resolution, is believed to be about $0.5 \times 10^9$ daltons. It is believed that the new technique can also resolve particles larger than $1.2 \times 10^9$ daltons. Another important advantage is that in the new technique resolution is much less dependent on electric field intensity; consequently, the new kind of electrophoresis can be run at much higher speed, so long as heat produced can be effectively dissipated. As a result, a typical laboratory run can be carried out in 4 to 8 hours, while corresponding runs using prior art techniques require 12 to 100 hours. Another significant advantage of the new technique is that larger amounts of sample, as compared to the known prior art, can be used, thus giving increased resolution and sensitivity. A further advantage is that the new technique can simultaneously resolve, in the same gel, particles from a wider mass range than is believed possible with prior art techniques. As a nonlimiting example, the new technique can resolve simultaneously, in the same gel, particles ranging in mass from about $10^6$ to about $10^9$ daltons. With previously known techniques several different gel concentrations would have been required to resolve particles in the narrower mass range from about $10^6$ to about $10^8$ daltons. As yet another important aspect of the invention, a technique has been found to minimize handling damage to cell-derived macromolecules by lysing cells or spheroplasts in a block of gel which is the same as, or compatible with, the electrophoresis gel, and implanting the entire block in the electrophoresis chamber.

These and other advantages of the invention, as well as additional inventive features, will become apparent from the detailed description which follows.

BRIEF DESCRIPTION OF THE DRAWINGS

FIG. 11 is similar to FIG. 10 but illustrates the hypothesized effect of an electric field which has a substantial intensity gradient in a direction transverse to the field direction.

FIG. 12 illustrates the circulation of cooled buffer through the electrophoresis chamber.

FIG. 13 illustrates the resolution obtained in an experimental example using the new kind of electrophoresis.

FIG. 14 is a perspective view of a mold used for lysing cells or spheroplasts in situ in gel blocks which are later inserted into matching wells in the electrophoresis gel.

DETAILED DESCRIPTION OF THE INVENTION

Figure 1:
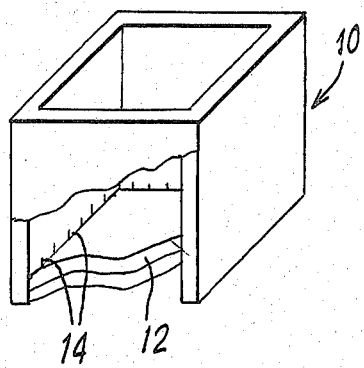
FIG. 1 is a perspective, partly cut-away view of an electrophoresis chamber useful in explaining certain principles of the invention.
Figure 2:
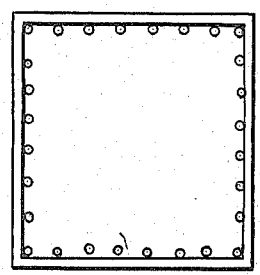
FIG. 2 is a top plan view of the same chamber.

An exemplary laboratory device useful in explaining certain principles of the invention is illustrated in FIG. 1 in a perspective, partly cut-away view, and in FIG. 2 in a top plan view. It comprises an open-top, rectangular electrophoresis chamber 10 made of an electrically insulating material, such as ¼" plexiglass, with dimensions approximately 4"×4". It supports on its bottom a layer of a medium 12, such as the agarose gel commonly used in electrophoresis, surrounded by electrodes 14. The electrodes are thin (0.032") platinum wires which extend vertically about ¾" each and are arranged about 1.5 cm apart as seen in the top plan view of FIG. 2.

Figure 3:
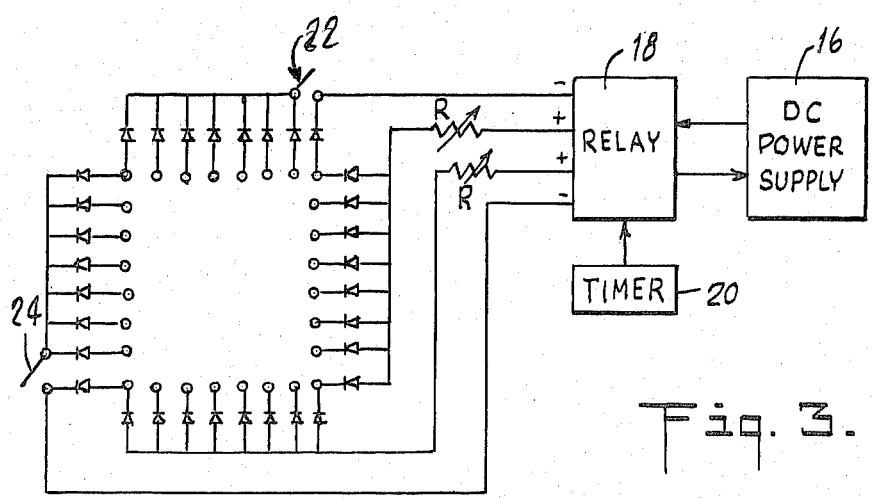
FIG. 3 is a partly schematic and partly block diagram showing an interconnection of exemplary chamber electrodes.

As one example, the electrode wires can enter the chamber through respective holes arranged in a horizontal row about ¾" above the interior bottom of the chamber, with each wire extending down, along a respective interior side wall, to the interior bottom of the chamber. In order to generate the desired electrical fields, electrodes 14 are interconnected as shown in FIG. 3. In particular, a d-c power supply 16 (such as Biorad Model 500) supplies d-c power to relay 18 (such as a DPDT, 115 volt a-c relay) which is controlled by a programmable timer 20 (such as a Lindberg Enterprises Chrontrol 4-Channel CT Series) to connect a selected one of its two pairs of outputs to the d-c power from supply 16. One output pair of relay 18 (consisting of a negative and a positive output terminal) is connected to the top and bottom rows of electrodes 14 (as seen in FIG. 3), through a respective diode for each electrode. However, it is only when a switch 22 is closed that all the electrodes of the top row are connected to the negative output terminal of relay 18; when switch 22 is open, only the rightmost electrode 14 is so connected. The other pair of relay 18 output terminals is similarly connected to the left and right rows of electrodes 14, using a similar switch 24 for the corresponding purpose. Variable resistors R can be used to vary the relevant voltages, as can the controls of power supply 16. The controls of timer 20 determine when a particular pair of relay 18 terminals is energized and when it is de-energized.

Figure 4:
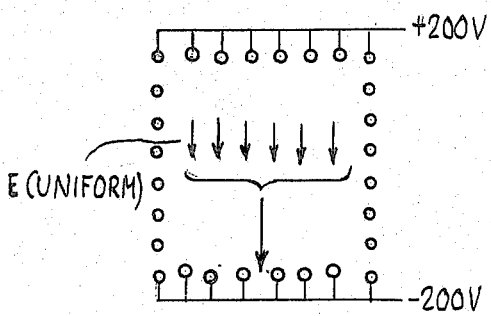
FIGS. 4–7 illustrate exemplary electric fields acting in the electrophoresis chamber.

When switch 22 is closed and the relay outputs energizing the top and bottom rows of electrodes 14 are on, e.g., at +200 and −200 volts respectively, a substantially uniform electrical field E is established across the bottom of the electrophoresis chamber, as illustrated schematically in FIG. 4. The short arrows in FIG. 4 are uniform in length, to indicate the substantial uniformity of the field, and the longer arrow indicates the general direction of the field (from positive to negative electrodes).

While in reality the field is not perfectly uniform in intensity throughout the gel, because of the physical arrangement of individual, spaced-apart electrodes, and for other reasons, and while the general direction may deviate somewhat from the vertical (as seen in FIG. 4), for the purposes of this specification such fields will be called uniform, and are distinguished from fields which are deliberately made nonuniform, e.g., by means of causing an operatively significant intensity gradient in a direction transverse to the overall field direction.

Figure 5:
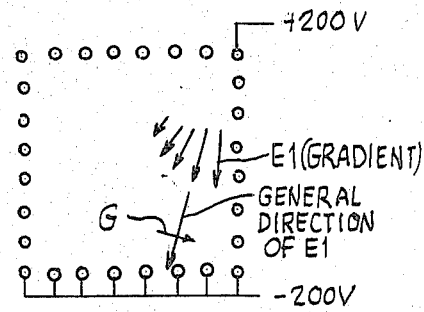

A field E1 which is nonuniform, in that it has an operatively significant intensity gradient in a direction transverse to the general field direction, is illustrated in FIG. 5, and is obtained, in this example, by opening switch 22 such that only the electrode in the upper righthand corner of FIG. 5 remains at the +200 V potential, while each of the bottom electrodes is at the −200 V potential. The electric field illustrated in FIG. 5 is somewhat fan-shaped, but still has a general direction, illustrated by the longer arrow, which can be viewed as the vector sum of the individual fields that are due to the respective potential differences between the upper right-hand corner electrode and the individual electrodes of the bottom row. The intensity gradient of interest is in a direction transverse to the general field direction, as shown by arrow G, and is due to the fact the distance between the upper righthand corner electrode and the electrodes of the bottom row increases (and the intensity per unit volume or unit area of the individual fields hence decreases) as one moves to the left along the bottom row, as is indicated by the decreasing lengths of the shorter arrows.

Figure 6:
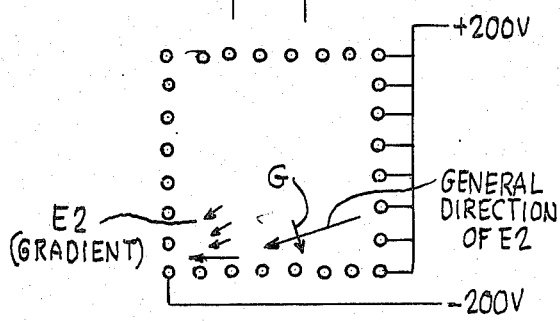

Similarly, when switch 24 is open and the relay outputs connected to the electrode at the lower left corner and the electrodes along the right-hand row are energized, a similar field E2 is generated, as illustrated in FIG. 6. The only significant difference between the fields in FIG. 5 and FIG. 6 is that the one in FIG. 6 has a different general direction, which is transverse to that of the field E1 in FIG. 5.

Figure 8:
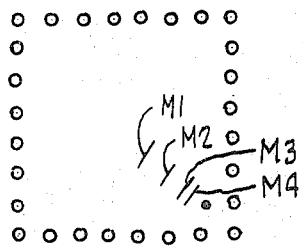
FIG. 8 illustrates the movement of particles in the new kind of electrophoresis.

One of the unexpected discoveries which this invention utilizes is that if fields such as E1 and E2 alternate out of phase with each other between respective high and low intensities at frequencies selected on the basis of the mass of the particles (e.g., macromolecules) which are to be separated electrophoretically, the particles move from an initial position, such as at 26, in an overall direction D which is transverse to both fields E1 and E2, and for any one particle the velocity of movement depends on its mass (or charge). As a result, particles of different masses (charges) travel different distances from the initial position 26, forming bands such as M1, M2, M3 and M4 in FIG. 8, where lighter particles move further distances from the initial position.

Figure 7:
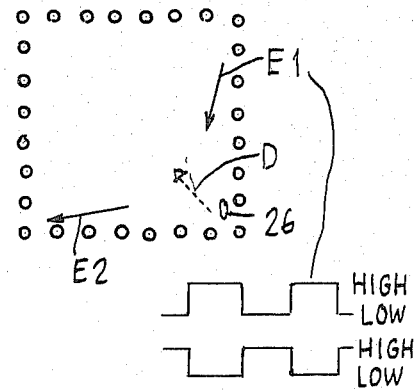

It should be noted that the term "transverse" as used in this specification is not limited to an angle of, or close to, 90°, but includes other substantial angles of intersection. When used with respect to the angle between electric fields such as E1 and E2, it is meant to exclude only those angles between electric fields in the prior art which resulted from spurious events or from the inability to achieve in practice the design goal of a uniform and unidirectional combination of fields. When used with respect to the angle between the overall direction of particle movement, the term "transverse" is again meant to exclude only angles which resulted from spurious events or from the inability of prior art devices to have the electrophoretic movement coincide with the desired field direction. The term "operationally significant" intensity gradient means here a gradient which is sufficient to enable the relevant fields to move the relevant particles in the direction transverse to the general field directions, for example, as illustrated in FIG. 7.

Satisfactory results can be obtained in some cases with electric fields which alternate and are transverse to each other as discussed above, but are substantially uniform, as is field E in FIG. 4. However, typically better results are obtained when one of the fields has the requisite intensity gradient in the direction transverse to its general direction. Typically, better results are obtained when both fields have such intensity gradients.

Figure 9:
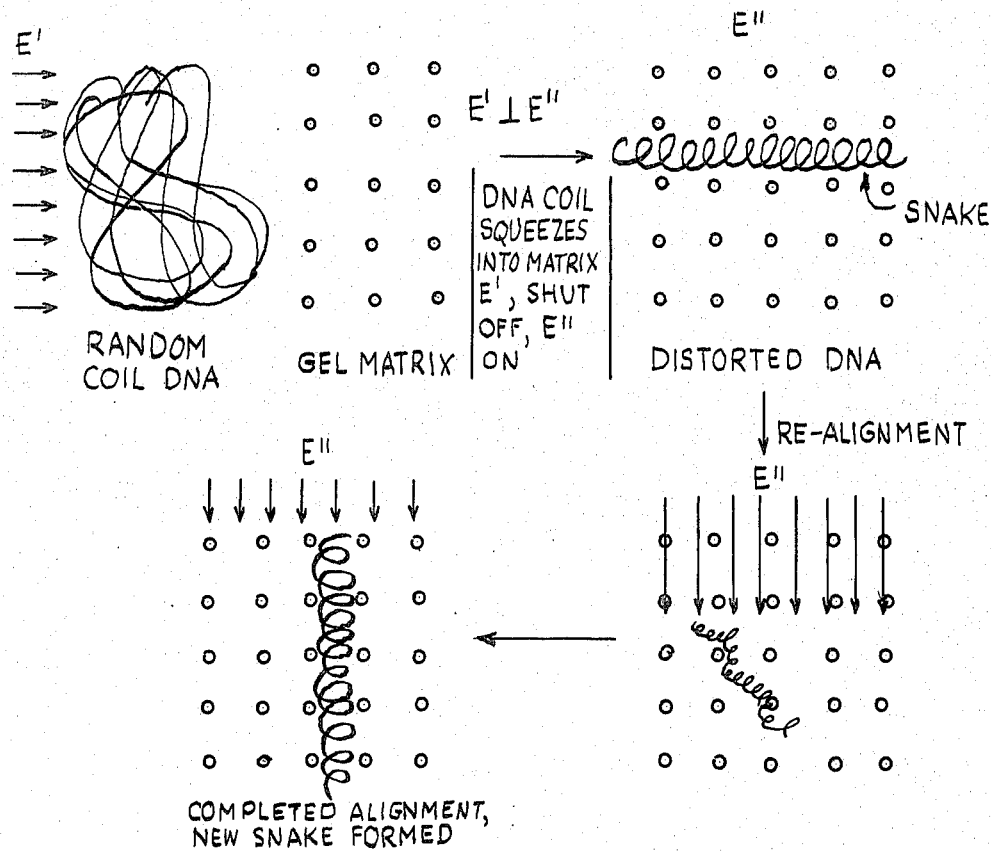
FIG. 9 illustrates a hypothesized distortion and movement of a large DNA molecule through agarose gel under the influence of transverse electric fields acting out of phase.
Figure 10:
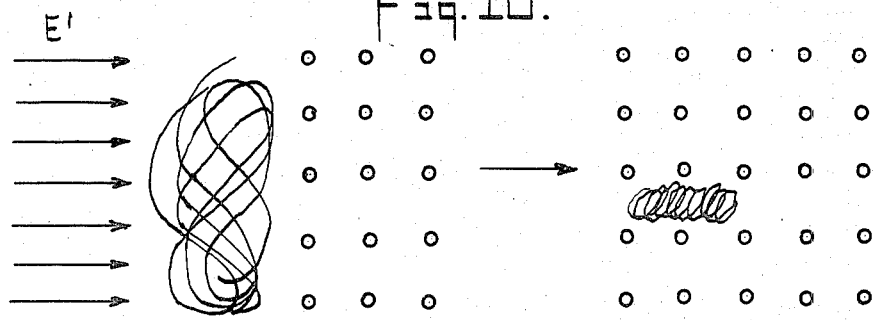
FIG. 10 illustrates the hypothesized effect of a uniform electric field on a large DNA molecule in agarose gel.

While the mechanism by which the new type of electrophoresis works is not entirely understood, it is believed that the application of alternating fields causes a large particle, such as a coiled DNA molecule, to squeeze into the agarose matrix by orienting itself first along the general direction of one of the fields, then along the general direction of the other, etc. Moreover, it is believed that using gradient fields (such as E1 and E2) rather than uniform fields (such as E) produces a shearing effect that helps stretch the molecule in the desired direction. FIG. 9 illustrates this hypothesis by showing a randomly coiled DNA molecule which is pushed into an agarose gel matrix by a uniform electric field E' and is squeezed into the gel by being formed into an elongated cylindrical shape (snake). This snake is then subjected to a uniform electric field E" and is gradually distorted away from its initial snake shape until it forms a new snake, this time oriented along the general direction of field E", etc., so that its overall direction of movement is along the approximate vector sum of the directions of fields E' and E". This initial hypothesis has been modified, however, by a later belief that long chain macromolecules such as DNA probably do not snake when their radius of gyration is greater than the effective gel pore radius. Instead, such macromolecules probably condense to a shape more akin to a "beer can" than a snake, as is illustrated in FIG. 10, and therefore do not move easily in a direction transverse to the long axis of the "beer cans." Indeed, it is believed that the use of a gradient rather than a uniform field is one of the critical factors for forcing large molecules, such as DNA molecules, into the desirable elongated cylindrical or snake shape, as is illustrated in FIG. 11. Moreover, it is believed that the proper choice of a frequency at which the change from one field to another should occur, is related to the time it takes the particle (molecule) of interest to orient itself into the desired elongated cylindrical or snake shape, and that this time t is related to the mass of the particle (the molecular weight) M, the effective pore radius of the gel r, and the measured velocity of the particle in the gel v, in accordance with the relationship $t \propto M^{1.5}/(r^2 v)$.

It should be emphasized that the hypothesis referred to above, while consistent with experimental results to date, is not to be taken as a factor limiting the scope of the invention, as the invention produces its beneficial results despite the fact that the underlying phenomenon may not be well understood, and despite the possibility that a totally different mechanism may be involved.

The following examples demonstrate certain aspects of the invention but, of course, should not be taken as limiting its scope:

General Electrophoretic Conditions for EXAMPLES A, B and C.

Gels about 1 cm thick were cast in 10 cm² disposable square Petri dishes. Wells for the sample were formed in a conventional manner using a plastic comb with teeth 0.250"×0.0787", spaced 0.125" apart. The gels consisted of 1.5% low endoosmosis agarose (Miles Biochemical Company) dissolved in TBE (10.3 g Tris, 5.5 g boric acid and 0.93 g disodium EDTA per liter). Electrophoresis buffer (TBE) was continuously circulated via a magnetically driven polypropylene-housed vane pump (Fischer Scientific) and cooled in a re-circulating refrigerated bath (Haake, type T-52), as illustrated in FIG. 12. The intake and discharge ends of the circulation pipes were close to the gel, and delivered and withdrew liquid buffer at two diametrically opposite corners of the gel square. Samples were loaded into wells using a Gilson Pipetman with the pippette tip ends cut to minimize shear. DNA was visualized after soaking gels in 0.5 micrograms of ethidium bromide per ml of TBE. Photographs were taken using Polaroid 107 film with shortwave U.V. illumination. Exposure times varied from 15 to 180 seconds at f8 depending on samples.

EXAMPLE A: Preparation and Electrophoresis of Marker DNA

Bacteriophage viruses T7, T2, and G were prepared by lysing a given amount of virus overnight at 50° C. in NDS as described in Laurer et al., Journal of Microbiology, 1975, 95: 309–326. The resulting lysates were then dialysed overnight against the electrophoresis buffer. The bacteriophage DNA masses in daltons are believed to be: $T7=2.7\times10^7$; $T2=1.2\times10^8$; and $G=5\times10^8$. A 0.02 microgram sample of each DNA was loaded into the wells in 5 microliters of 10% glycerin, TBE and 0.0015% bromphenol blue. Samples were run into gel with a single field for 15 minutes before pulsing. Optimal pulse times, in seconds, for resolution of macromolecules near or at the molecular weight of the following examples were T7=0.25; T2=4; and G=20. The term "pulse time" refers to pulse width, i.e., the time interval over which one of the fields is on (or high) while the other one is off (or low). In this experiment fields of the type and voltage levels illustrated in FIGS. 5 and 6 were used, i.e., both fields had intensity gradients. The relative mobility obtained in this experiment was G=1; T2=2.5; and T7=8.

EXAMPLE B: Yeast DNA

Various strains of yeast were grown to mid-log phase in 100 to 1000 ml of YPD (YPD: 1 g yeast extract, 2 g dextrose and 2 g bactopeptone added to 1 liter of distilled water). Spheroplasts were made as described in Cryer et al., *Progress in Cell Biology*, Vol. 12, 1975, pp. 39-44. The spheroplasts were then lysed in NDS overnight at 50° C. Yeast lysates were prepared in NDS with concentrations ranging from about $10^9$ to $2 \times 10^{10}$ cells per ml of lysate. Generally, 90 microliters of lysate were loaded using a blue-tipped (1 ml capacity) Pipetman. Samples were run into 1.5% agarose gel at 100 volts for 45 minutes with a single field. Pulse times of 15-45 seconds at 200 volts (fields E1 and E2 of FIGS. 5 and 6) gave the molecular weight resolutions shown in reduced scale in FIG. 13.

EXAMPLE C: Ethidium Bromide

The experimental conditions of Example B were used, except that gels were run in the dark and contained 0.5 micrograms per ml ethidium bromide in the gel as well as the circulation buffer, and pulse times were 30 and 45 seconds, using D-273 yeast lysates. Clear resolution of many chromosomes was obtained.

In the examples above, lysing was done in a conventional manner and the lysates were transferred to the electrophoresis gel in a conventional manner. It is known that such handling of lysates can result in breakage and other damage to fragile macromolecules. A way has been found, however, to substantially avoid such deleterious effects, and it forms a part of this invention. In particular, in accordance with the invention cells or spheroplasts (cells minus cell walls) can be suspended in agarose gel, and this gel can be poured into molds to form inserts. The inserts are then placed in lysing solution to lyse the suspended cells or spheroplasts, and then the intact inserts are placed snugly into matching wells in the electrophoresis gel. The gel making up the inserts can be the same as, or compatible with, the electrophoresis gel.

An illustrative mold used in this new technique is shown in a perspective view in FIG. 14, and comprises a pair of matching rectangular blocks 14a and 14b which can be secured in the illustrated configuration by means of screws 14c. The top block 14a has a number of molding channels 14d which go through the entire thickness of the block, while the bottom block 14b is solid. When the blocks are assembled in the configuration shown in FIG. 14, suitable agarose gel with suspended cells or spheroplasts is poured into the molding channels 14d and allowed to solidify. The blocks 14a and 14b are then taken apart, and the insert blocks, such as 14e, are carefully extracted, placed in lysing material under conditions sufficient for staisfactory lysing, and are then carefully inserted snugly into matching wells formed in the electrophoresis gel, e.g., by a comb whose outer shape and dimension matches the molding channels 14d. The following Example D illustrates electrophoresis using the new technique.

EXAMPLE D: Lysing In Gel Inserts

Yeast spheroplasts ($10^{10}$ to $10^{11}$ cells per ml of 1% low gelling agarose in TBE) were suspended in agarose gel and poured into the mold channels to form inserts. The inserts were then placed into NDC at 50° C. overnight, thereby lysing the suspended spheroplasts. Yeast cells, previously treated with mercaptoethanol were also suspended in 1% agarose gel, but in this case 75 microliters of a Zymolyase 5000 mixture (2 mg per ml 0.01M sodium phosphate, 50% glycerine) was added to the inset mixture prior to molding the inserts. 75 microliters of Zymolyase was also added to 0.8 ml of LET (0.5M tetrasodium EDTA, 0.01M Tris, pH=7.5). Molded inserts with the yeast cells were added to the LET, and incubated overnight at 37° C. The resulting suspended spheroplasts were then lysed in NDS. Both cell and spheroplast inserts were placed in matching wells in electrophoresis gel. Electrophoresis using the conditions discussed above in connection with Examples A-C, provided good chromosomal DNA resolution.

EXAMPLE E: Double Minute DNA $2.5 \times 10^7$ mouse 3T3-R500 cells were lysed in 0.3 ml of NDS at 50° C. for four (4) days. The lysate were then loaded into 1.5% agarose cells in TBE and run at 200 Volts with 30 second pulsing. One diffuse band was obtained. It moved as if it had the molecular weight of intact double minute DNA (mol. wt. approx. $600 \times 10^6$). Marker was G phage (mol. wt. approx. $500 \times 10^6$).

The new kind of electrophoresis discussed above has numerous applications. As one example, by use of this technique yeast chromosomal DNA has for the first time been successfully separated and characterized by size. Another use of the new technique is exploring the nature of DNA-gyrase complexes in *E. coli* supercoiled, chromosomal domains to map gyrase locations and thus provide tools for eucaryotic chromosome analysis. The new technique is particularly advantageous when different molecules, such as different DNA molecules, are close to each other in mass. The use of alternating fields each with an intensity gradient, tends to sharpen resolution dramatically and allow unexpected resolution for molecules close to each other in mass. Another use is resolving a great number of bands in the same gel, an important consideration when eucaryotic DNA is being analyzed. Yet another use of the new kind of electrophoresis is to purify molecules such as enzymes, e.g., urokinase, myosins or hyaluronic cids so as to provide a purified sample which can serve as the basis for developing a way to produce the same or an equivalent molecule. As yet another use, the effect of various agents, such as drugs, can be assessed for their effect on chromosomes, nucleic acids and proteins because of the ability to separate such materials provided by the invention. As yet another example, polymers can be accurately and quickly analyzed for molecular weight distribution, branching, and other physical properties by use of the new kind of electrophoresis. As still another example, intact or cut human, animal or plant chromosomes can be analyzed using the new kind of electrophoresis.

It should be clear that the laboratory device discussed in connection with FIGS. 1-8, and the particular kinds of electric fields used thereby, and the insert molding device discussed in connection with FIG. 14, are only specific examples which are convenient for explaining certain principles of the invention. Numerous variations are possible and are within the scope of the invention. For example, a differently shaped electrophoresis chamber, or differently produced, distributed or varied electric fields can be used so long as the particles are acted on by electric fields varying with time so as to move them in overall directions generally transverse to at least two of the relevant, operationally significant fields. For example, the desired fields can be generated by differently shaped electrodes, by suitably excited coils or by other sources or combinations of different (in kind) sources, and the relevant field directions can be controlled by other means, such as without limitation, changing the net direction of the field or changing the electrode characteristics (e.g., potential). Similarly, the desired field gradient can be produced in any number of ways, such as by selecting an appropriate shape for the relevant electrodes, by maintaining different electrode portions at different potentials or by the interaction of two or more fields. Moreover, more than two fields can be used, so long as the net effect is at least to act in the desired manner on a particle first in one direction, then in another direction transverse to the first, etc., so as to move the particle in a third direction transverse to the first two.

It has been found desirable, in the above-described preferred exemplary embodiment of the new electrophoresis device, to have a number of discrete electrodes, and to interconnect them through devices (such as diodes) which allow current flow to each in only a selected direction. Moreover, it has been found desirable to have the wire electrodes extend along the interior sidewalls of the chamber vertically, or nearly so, because such electrodes make it particularly convenient to generate the desired electrical fields, and because with such electrodes when they are long enough in the vertical direction it is possible to have several gel layers on top of each other, each containing samples of particles, and to subject all of them to substantially identical electric fields so as to carry out electrophoresis in all of them concurrently. To generate more complex fields, or to provide more freedom of choice in producing fields of selected characteristics, such as the fields E, E1 and E2 in FIGS. 4-6, each electrode (or at least electrode of a selected plurality of electrodes) can have its own, switchable, power supply connection such that each can be selectively maintained at any positive or negative electrical potential within a selected range (or at ground). In some cases, as few as three electrodes will suffice, and two of them can be connected (intermittently) to the same potential, so long as they cooperate with each other to produce at least two electrical fields which have the desired characteristics (i.e., being transverse to each other).

As one variation, the new kind of electrophoresis arrangement described above can make use of high frequency switching between transverse fields, e.g., at frequencies in the range from about $10^6$ to about $10^9$ Hz, superimposed on one or more steady, or more slowly switching fields such as the fields E, E1 and E2 discussed above. It is believed that the rapidly switching field or fields can help rotate (or orient) particles such as macromolecules in a desired manner while the steady or slowly switching field or fields can serve to move the particles in the desired overall direction. This arrangement of rapidly switching fields and steady or slowly switching fields can in fact use as few as two transverse fields, at least one of them having a steady or slowly switching intensity component and a rapidly switching intensity component superimposed thereon. For example, mutually transverse fields E1 and E2 as in FIG. 7 can be used, but at least one of the electrodes can have superimposed on the illustrated squarewave voltage waveform, a much higher frequency voltage waveform of a selected amplitude, such as at a frequency from about $10^6$ to about $10^9$ Hz.

What is claimed is:

1. An analytical electrophoresis method of separating particles which is capable of separating at least large DNA molecules and comprises subjecting said particles in a suitable medium to at least two electric fields varying with time and having generally co-planar overall directions which are transverse to each other, to move the particles in an overall direction generally co-planar with but transverse to the respective overall directions of said fields to achieve high resolution analytical electrophoresis separation of said particles into a pattern of bands.

2. A method as in claim 1 in which at least one of the fields has an intensity gradient in a direction transverse to and generally co-planar with its overall direction for at least a portion of the time it acts on the particles.

3. A method as in claim 1 or 2 in which said at least two fields vary by alternating between respective low and high intensities out of phase with each other.

4. A method as in claim 3 in which the timing of said alternating is related to the mass of the particles to be separated.

5. A method as in claim 1 in which said fields acting on the particles to cause them to move vary with time as a function of the mass of the particles raised to the power of about 1.5.

6. A method as in claim 1 in which the particles are polypeptide molecules.

7. A method as in claim 1 in which the particles are myosin or hyaluronic acid molecules.

8. A method as in claim 1 in which the particles are nucleic acid molecules.

9. A method as in claim 8 in which the nucleic acid molecules are DNA molecules.

10. A method as in claim 1 in which the particles are chromosomes.

11. A method as in claim 10 in which said chromosomes are derived from a eucaryote.

12. A method as in claim 1 in which the particles are human chromosomes.

13. A method as in claim 1 in which the particles are animal chromosomes.

14. A method as in claim 1 in which the particles are plant chromosomes.

15. A method as in claim 1 in which the particles are yeast chromosomes.

16. A method as in claim 1 in which the particles move in a gel medium having an effective pore size less than the size of the particles.

17. A method as in claim 16 in which the particles being separated are obtained by lysing whole cells or spheroplasts in an insert of the same or a compatible gel which is thereafter placed in said gel medium and in which said electrophoretic separation is carried out without first separating said particles from the lysed whole cells of spheroplasts.

18. A method as in claim 1 in which said medium is a layer of gel and including the step of suspending whole cells or spheroplasts in the same or compatible gel material and solidifying the suspension into a solid insert, lysing the cells or spheroplasts without removing them from the solidified gel insert, and thereafter placing the lysed insert into a matching well in said layer of gel and subjecting it to said electric fields, and wherein at least one of said fields has an intensity gradient along the gel layer.

19. A method as in claim 1 in which said medium has a pore size less than the particle size and the action of said electric field on the particles repeatedly changes the molecular configuration of the particles to cause them to move through said medium.

20. A method as in claim 1 including controlling said field for selective sharpening of a selected part of said pattern of bands.

21. A method of detecting or diagnosing genetic phenomena correlated with variations in the molecular weight of chromosomes, nucleic acids or proteins comprising separating the chromosomes, nucleic acids or proteins into an analytical electrophoresis band pattern by subjecting them to electric fields which have overall directions transverse to and generally co-planar with each other, at least one of which has a field intensity gradient transverse to and generally co-planar with its overall direction, and wherein the respective intensities of the fields are varied over time periods which are out of phase as between respective fields and are related to the molecular weight of the chromosomes, nucleic acids or proteins to be separated.

22. An apparatus for analytical electrophoresis comprising:
a support for a medium in which one or more samples of particles to be separated can be placed;
means for generating electric fields which act on the particles along respective different overall directions transverse to and generally co-planar with each other and for causing at least one of the fields to have an intensity gradient transverse to and generally co-planar with its overall direction; and
means for repetitively varying selected characteristics of the respective fields over time periods which are out of phase as between different fields and are related to the mass of the particles to be separated, to move the particles in an overall direction transverse to and generally co-planar with the respective overall direction of each of two varying fields and thereby separate said particles into an analytical electrophoresis band pattern.

23. Electrophoresis apparatus as in claim 22 in which the field generating means comprise at least three discrete electrodes spaced apart from each other and means for maintaining the respective electrodes at respective independently selectable potentials for respective selected time periods.

24. An apparatus for analytical electrophoresis comprising:
a support for a layer of medium in which one or more samples of particles can be placed for separation into an analytical electrophoresis band pattern along the plane of the layer;
at least three electrodes spaced from each other and arranged at selected positions to contact the medium; and
means for maintaining the respective electrodes at respective independently selectable electrical potentials for respective selected time periods to effect said separation of the particles into an analytical electrophoresis band pattern.

25. An electrophoresis apparatus as in claim 24 in which the means for maintaining the electrodes at respective potentials comprise means for causing the electrodes to generate at least two electrical fields having a selected characteristic varying out of phase as between the two fields, said fields having overall directions transverse to each other in the layer plane and causing the particles to move in a third overall direction which is along the layer plane and is transverse to the respective overall directions of said fields.

26. An apparatus as in claim 25 in which the means for causing the electrodes to generate said at least two electric fields comprise diode connections between the at least three electrodes which are switchable to selectively energize selectable combinations or subcombinations of electrodes to thereby control the intensity, uniformity and/or gradients of said fields.

* * * * *